United States Patent [19]

Feinland et al.

[11] 4,054,413

[45] * Oct. 18, 1977

[54] AUTOXIDIZABLE HAIR DYE CONTAINING PREPARATIONS

[75] Inventors: Raymond Feinland, Stamford, Conn.; Sigmund Iscowitz, Flushing; Milos S. Bil, Forest Hills, both of N.Y.

[73] Assignee: Clairol Incorporated, New York, N.Y.

[*] Notice: The portion of the term of this patent subsequent to Nov. 18, 1992, has been disclaimed.

[21] Appl. No.: 570,675

[22] Filed: Apr. 23, 1975

Related U.S. Application Data

[63] Continuation-in-part of Ser. No. 489,317, July 17, 1974, Pat. No. 3,920,384.

[51] Int. Cl.$^2$ ............................................. A61K 7/13
[52] U.S. Cl. ................................... 8/10.2; 8/11; 8/32; 424/70
[58] Field of Search .......................... 8/10.2, 11, 32

[56] References Cited

U.S. PATENT DOCUMENTS

| | | | |
|---|---|---|---|
| 2,162,458 | 6/1939 | Lehmann | 8/10.2 |
| 2,733,186 | 1/1956 | Brye | 8/10.2 |
| 2,975,101 | 3/1961 | Charle et al. | 8/10.2 |
| 3,167,478 | 1/1965 | Charle et al. | 8/10.2 |
| 3,337,411 | 8/1967 | Wilmsmann | 8/10.2 |

FOREIGN PATENT DOCUMENTS

| | | | |
|---|---|---|---|
| 12,902 | 4/1900 | United Kingdom | 8/10.2 |

OTHER PUBLICATIONS

Noller, Chemistry of Organic Compounds, W. B. Saunders Company, Philadelphia (1957), pp. 167-171.
Chemical Abstracts, vol. 74, 12300p. (1971).

*Primary Examiner*—Albert T. Meyers
*Assistant Examiner*—Vera C. Clarke
*Attorney, Agent, or Firm*—Irving Holtzman; George A. Mentis; David J. Mugford

[57] ABSTRACT

An autoxidizable hair preparation capable of coloring hair when applied thereto and exposed to the atmosphere comprising N,N-bis(2-hydroxyethyl)-p-phenylenediamine or an acid addition salt thereof and a triol selected from the group consisting of 1,2,4-benzenetriol and 2,4,5-trihydroxytoluene. The preparation is applied at multiple spaced intervals of time until the desired color build-up is attained. Also prepares the composition by preforming a solution of the triol by storing the corresponding triacetate in acid solution for a period of time then adding the N,N-bis(2-hydroxyethyl)-p-phenylenediamine.

6 Claims, No Drawings

AUTOXIDIZABLE HAIR DYE CONTAINING PREPARATIONS

RELATED CASES

This application is a continuation-in-part of application Ser. No. 489,317, filed July 17, 1974, now U.S. Pat. No. 3,920,384.

This invention relates to a process for gradually coloring hair over a relatively long period of time using, as the coloring agent, autoxidizable organic compounds. It also concerns certain compositions of matter that are useful for this purpose and a method for preparing these compositions.

It is known in the prior art that human hair can be colored over a period of time through the use of certain lead salt compositions. However, these lead salt compositions (so-called "color restorers") have an inherent limitation in the shade quality that can be achieved with them. This is a weak yellow or yellow-orange coloration and is dependent on the formation of lead sulfide. Furthermore, lead salts are known to be highly toxic when ingested and therefore, do present some hazard in use.

It has now been found that a gradual coloration of the hair over a period of time, and particularly grey hair, may be effectively accomplished by means of repeated applications of a composition containing autoxidizable organic compounds in solution. These materials may also be incorporated in a composition which can also serve as a hair grooming agent so that the hair may simultaneously be colored and groomed during the application of these compositions.

It is accordingly an object of the present invention to provide a safe method for gradually coloring hair over a period of time.

It is also an object of the present invention to provide a composition that is useful in carrying out the aforesaid process.

It is a further object of this invention to provide a method for preparing said composition.

Other and more detailed objects of this invention will be apparent from the following description and claims.

It has been found, in accordance with the present invention, that an autoxidizable hair coloring composition giving natural looking, drab and long-wearing hair color can be otained by employing a composition comprising a mixture of N,N-bis(2-hydroxyethyl)-p-phenylenediamine or an acid addition salt thereof (e.g., sulfate, chloride, etc.) and 1,2,4-benzenetriol. In place of the said benzenetriol, there may also be employed 2,4,5-trihydroxytoluene. It has been further found that after the desired drab color is developed on hair through the use of these compositions, the hair maintains these desired drab shades for relatively long periods of time even on exposure to the air.

Several references in the prior art have suggested the use of benzenetriols in hair coloring compositions. In this connection, attention is invited to U.S. Pat. Nos. 2,162,458; 3,214,472; 3,236,734; 2,733,186; 2,975,101; 710;134; 754; 948; 754,949; 745;532; 824,519; 827,439. Other references of interest relating to the hydrolysis of 1,2,4-triacetoxybenzene are as follows: Ber. 31, (1898) p. 1247; Ber. 32 (1899) p. 282 and J.C.S. 1934 p. 1625. However, none of these references suggest the claim compositions or processes.

To compare the relative merits of autoxidation dyeing properties of the present compositions on hair samples as to depth of shade and the lasting qualities of the colorings, the experiments described below were carried out. The results obtained with the present composition were compared with the results obtained from the autoxidation of the individual components of this composition (i.e., N,N-bis(2-hydroxyethyl)-p-phenylenediamine sulfate or 1,2,4-benzenetriol) or compositions containing other oxidation intermediates. The following test conditions were employed in this study:

a. All the compositions employed were aqueous solutions containing 0.014M of each test compound, 0.03% sodium sulfite, and 1.5% triethanolamine; the pH of each composition was adjusted to 8 using sulfuric acid.

b. Gray hair swatches were impregnated with each composition four times at room temperature (twice a day for 2 days), then shampooed, rinsed and air dried. Color readings were taken immediately and again after exposure of the swatches to the atmosphere for 4 months.

c. The color readings of L, a, b were obtained with Hunter Color/Difference Meter D25D2.

The results of these tests are summarized in the Table below. The color results are given visually as well as in Hunter units L, a, b where L is lightness (0 = black, 100 = white), $+a$ is red, $-a$ is green, $+b$ is yellow and $-b$ is blue.

The abbreviations in the Table have the following significance:

BHE = N,N-bis(2-hydroxyethyl)-p-phenylenediamine sulfate
PPD = p-phenylenediamine
PTD = p-toluenediamine sulfate
Benz T = 1,2,4 benzenetriol

TABLE I

| Compounds | L | a | b | Visual Observation |
|---|---|---|---|---|
| BHE, original | 29.1 | +0.8 | +8.2 | Light yellow brown |
| BHE, after 4 months | 28.8 | +1.4 | +7.5 | Slightly redder |
| PPD, original | 37.6 | +0.5 | +10.8 | Very light yellow brown |
| PPD, after 4 months | 28.3 | +1.9 | +6.8 | Redder and much darker |
| PTD, original | 37.0 | +1.7 | +10.6 | Very light orange brown |
| PTD, after 4 months | 29.8 | +4.0 | +9.0 | Much redder and darker |
| Benz T, original | 28.4 | +2.2 | +7.2 | Light red brown |
| Benz T, after 4 months | 29.3 | +2.6 | +7.0 | Unchanged |
| BHE + Benz T, original | 19.8 | −0.2 | +2.7 | Dark drab brown |
| BHE + Benz T, after 4 mos. | 20.6 | −0.3 | +2.8 | Unchanged |
| PPD + Benz T, original | 17.2 | +0.5 | +3.5 | Dark brown |
| PPD + Benz T, after 4 mos. | 17.4 | +1.4 | +3.2 | Slightly redder |
| PTD + Benz T, original | 17.7 | +0.7 | +3.7 | Dark brown |
| PTD + Benz T, after 4 mos. | 17.9 | +1.3 | +3.5 | Slightly redder |

As can be seen from Table I, the color produced with the combination of BHE and Benz T is drabber than the other combinations and remains drabber after exposure to the atmosphere for 4 months. It is therefore eminently suitable for use by men. BHE by itself is drabber than PPD or PTD initially and is much more stable after exposure to room air. Apparently, PPD and PTD continue to slowly oxidize after the swatch is shampooed which means that a person using either as an autoxidizable hair color would not know what the final color of his hair would be.

As noted previously, the use of benzenetriols in hair coloring compositions has been suggested in the prior art. In preparing compositions of this character, it has been recommended that the triol first be produced and then recovered as a solid after which it is to be incorporated in the hair coloring composition. However, the benzenetriols are extremely unstable in the solid state and this has mitigated against their previous use in commercial preparations. In this connection, attention is invited to "The Chemistry of Synthetic Dyes" by K. Venkataraman, Vol. 5, Chapter VII, pages 495–496, Academic Press Inc., New York, 1971.

It has now been found that autoxidizable hair dye compositions may be prepared by forming a solution of the triol by the acid hydrolysis of the corresponding triacetate in a solvent and then mixing this preformed solution with a p-phenylenediamine. The isolation of the triol as a solid and the attendant disadvantages which characterized the processes suggested in the prior art is thus avoided, e.g., low yield and premature autoxidation.

More particularly, this aspect of the present invention involves preforming the solution of a triol selected from the group 1,2,4-benzenetriol and 2,4,5-trihydroxytoluene by storing the triacetate of said triol at a temperature between about room temperature and 50° C for about 12 to 72 hours with a lower aliphatic alcohol (1 to 3 carbon atoms) and a concentrated inorganic non-oxidizing mineral acid, i.e., hydrochloric or sulfuric, and then mixing said preformed solution with a composition containing a p-phenylenediamine or an acid addition salt thereof. Of special interest are the p-phenylenediamines of the formula:

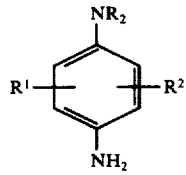

where R is hydrogen, 2-hydroxyethyl, or 2-hydroxypropyl, 3-hydroxypropyl; or 2,3-dihydroxypropyl and $R^1$ and $R^2$, which may be the same or different, are hydrogen or methyl; or the acid addition salts thereof.

By way of illustrating the lower aliphatic alcohols that may be employed in the aforesaid process, mention may be made of methanol, ethanol, n-propanol and isopropanol. To exemplify the p-phenylenediamines that are utilizable herein, the following are given: p-phenylenediamine, 2,5-diaminotoluene, N,N-bis (2-hydroxyethyl)-p-phenylenediamine, 2,6-dimethyl-p-phenylenediamine, and $N^4,N^4$-bis (2-hydroxyethyl)-2-methyl-p-phenylenediamine.

In the preferred embodiments of this aspect of the invention, about 1 to 60 parts (optimally 4 to 40 parts) of the triacetate and 0.5 to 2.0 parts of the conc. acid (sulfuric acid) are placed in 100 parts of ethanol (95 to 100%). This is preferably stored overnight at a temperature of about 50° C. This process is preferred because the solutions obtained are essentially colorless. This is important because color development during hydrolysis under other conditions is accompanied by oxidation of the triol; which oxidation of the triol is autocatalytic, i.e., the oxidation rate increases as the extent of the oxidation increases.

Because of the tendency of the triols to rapidly oxidize, they are preferably prepared just prior to use in preparing the present composition (e.g., by storing the triacetate at room temperature to 50° C for 12 to 24 hours with ethanol and concentrated sulfuric acid). Each triol is formed by transesterification as follows:

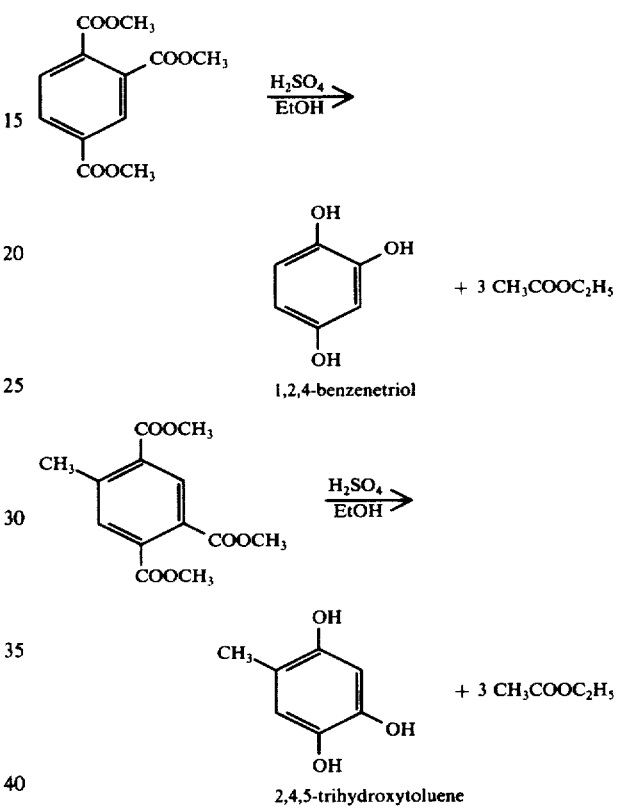

The reaction mixture is then added in its entirety without separation to the rest of the formulation, where the pH is adjusted with a suitable alkali.

The composition of the present invention is most conveniently applied in the form of a hair grooming composition which will simultaneously groom and color the hair. The autoxidizable compounds are usually contained in solution in the composition. In a typical application, enough composition is applied to thoroughly wet hair (approximately 15 g. on the average), followed by simple combing into the desired style. No shampooing or rinsing is required after application as is the case for the usual hair coloring product. The extent of the hair coloring is determined by the concentration of the autoxidizable organic compounds and the number of applications, the latter determined at the discretion of the user.

The quantity of N,N-bis(2-hydroxyethyl)-p-phenylenediamine sulfate and triol that may be employed may vary somewhat. In general, however, the former (i.e., BHE) will comprise between about 0.05 to 1.0% or 1.5% by weight and preferably between about 0.1 to 0.5% or 1.0% of the composition, while the latter (i.e. the triol) will comprise between 0.02% and 1.0% by weight and preferably between about 0.05 to 0.2% or 0.4%.

In addition to the reactive autoxidizable ingredients, the present composition will preferably contain a hair grooming agent. Some typical materials that may serve this purpose are the quaternized vinylpyrrolidone copolymers, carboxyvinyl polymers, etc. Plasticizers, conditioners and slip agents may also be chosen from a variety of compounds such as polyoxyethylene lauryl ether, polyoxyethylene fatty alcohol, stearyldimethylbenzylammonium chloride, silicone copolymer, etc.

The above ingredients are chosen to make a liquid or gel type of composition. For repeated use, an aerosol foam is particularly suitable since the ingredients are protected against degradation by air. Common Freons such as 12, 114 or 152A are suitable as well as hydrocarbon propellants.

The pH of the composition is ordinarily adjusted to the range 4 to 11 and preferably 6 to 8 with an alkalizing agent, e.g., ethanolamine, diethanolamine, triethanolamine, disodium hydrogen phosphate, sodium carbonate, etc.

An antioxidant is useful to prevent premature oxidation of the intermediates during shelf storage. This may be chosen from such chemicals as sodium sulfite, ascorbic acid, sodium hydrosulfite, etc. The level of antioxidant can vary between 0.03 to 1% to be determined by storage stability needs. The quantity and type of antioxidant also determine the rate of the haircoloring reaction.

Water is ordinarily the major constituent of the composition and can vary over a wide range dependent in large measure on the quantity of other additives. Thus, the water content may vary between 50 to 95%.

An alcohol, glycol or derivative thereof is added as a solubilizing agent in the range of 0 to 30% depending on the rest of the composition.

The following Examples are given to further illustrate the present invention. The following terms used in these Examples or elsewhere have the meaning ascribed to them below.

Gafquat 755: quaternized vinylpyrrolidone copolymer; has a minimum of 19% solids in a water vehicle and have an average M.W. over 1,000,000.

Emulphor AM 650: polyoxyethylated (10) isostearyl alcohol (10 moles of ethyleneoxide).

Brij 35: polyoxyethylated (23) lauryl ether (23 moles of ethyleneoxide).

Silicone SF-1066: dimethyl polysiloxane/polyethyleneoxide/polypropyleneoxide copolymer vis. 1200 - 1500 centistokes at 25° C.; s.g. at 20° C 1.04.

BHE: N, N, bis (2-hydroxyethyl)-p-phenylenediamine sulfate.

Propellant 152 a: 1, 1 difluoroethane.

Propellant 114: 1,2 - dichloro - 1,1,2,2-tetrafluoroethane.

Propellant 12: dichlorodifluoromethane.

Polymer JR: cationic polymer of hydroxyethyl cellulose.

Emulphogene BC 720: tridecyloxypoly(ethyleneoxy)12 ethanol.

Carbopol 941: A water soluble polymer of acrylic acid crossed linked with about 1% of a polyallyl ether of sucrose having an average of 5.8 allyl groups for each sucrose molecule (M.W. of the order of 1,000,000).

UCON-LB-1715: Polypropylene glycol butyl ether — viscosity is 1715 Saybolt universal seconds at 100° F.

UCONLB-3000: polypropylene glycol butyl ether — viscosity is 3000 Saybolt universal seconds at 100° F.

EXAMPLE 1, AEROSOL FOAM a. The triol is prepared by weighing 1.26 g. 1,2,4-benzenetriacetate, 30 g. ethyl alcohol (anhydrous), 0.4 g. conc. sulfuric acid into a container which should have little or no headspace remaining.
   Cap the container and place in a 50° C oven for 16 hours (approx.). A clear solution will result containing 0.63 g. triol, 1.323 g. ethyl acetate and excess alcohol. Set aside until step (h).
b. Mix at room temperature 140 g. water, 200 g. ethyl alcohol and 20 g. Gafquat 755 until uniform.
c. Mix at 50° C 0. 53 g. Emulphor AM 650, 0.40 g. Brij 35 and 0.13 g. perfume until a clear solution is obtained.
d. Add (b) to (c) and mix until uniform.
e. Add 0.67 g. stearyldimethylbenzylammonium chloride and mix until lumps dissolve.
f. Add 0.53 g. Silicone SF 1066 to batch and mix until uniform.
g. Add 1.47 g. of BHE and 0.60 g. sodium sulfite and mix until uniform.
h. Add triol solution and mix until uniform.
i. Adjust pH with triethanolamine to 7.8 – 8.1 (4 to 5 g.).
j. Q.S. with water to 1,000 g.

A clear, colorless solution is obtained with the following composition:

| | |
|---|---|
| BHE | 0.147% |
| 1,2,4-benzenetriol | 0.063 |
| ethyl acetate | 0.132 |
| sodium sulfite | 0.060 |
| triethanolamine | 0.4 |
| ethyl alcohol (95%) | 23 |
| Gafquat 755 | 2.000 |
| Emulphor AM 650 | 0.053 |
| perfume | 0.013 |
| stearyldimethylbenzylammonium chloride | 0.067 |
| Silicone SF-1066 | 0.053 |
| Brij 35 | 0.04 |
| water q.s. | 100.0 |

To 94 g. of above composition, 6.g. of a propellant blend of 152A/114/12 (30/35/35) is added to obtain a quick breaking aerosol foam.

The composition after being applied twice a day for 2 days (total of 4) to gray hair gives a natural-looking medium drab brown shade. In an alternative procedure, the above compositions after being applied daily for about 10 days give a natural-looking drab brown shade. No rinsing or shampooing is required after application in either procedure.

EXAMPLE 1A, AEROSOL FOAM a. The triol is prepared by weighing 7.56 g. 1,2,4-benzenetriacetate, 30 g. anhydrous ethyl alcohol (approx.), 0.6 g. conc. sulfuric acid into a container which should have little or no headspace remaining. Cap the container and place in a 50° C oven for 16 hours (approx.). A clear solution will result containing 3.78 g. triol, 7.938 g. ethyl acetate and excess alcohol. Set aside until step (g).
b. Mix at room temperature 564 g. water, 163 g. ethyl alcohol and 5 g. Polymer JR until dissolved and uniform.
c. Mix at 50° C 0.53 g. Emulphogene BC 720, 0.40 g. Brij 35 and 0.13 g. perfume until a clear solution is obtained.
d. Add (b) and (c) and mix until uniform.

e. Add 0.67 g. stearyldimethylbenzylammonium chloride and mix until lumps dissolve.
f. Add 11.04 g. of BHE, 0.90 g. sodium sulfite and 1.00 g. E.D.T.A. disodium salt and mix until uniform.
g. Add triol solution and mix until uniform.
h. Adjust pH with triethanolamine to 6 – 6.2 (2.5 to 3.5 g.).
i. Q.S. with water to 1,000 g.

A clear, yellow solution is obtained with the following composition:

| | | |
|---|---|---|
| BHE | | 1.104% |
| 1,2,4-benzenetriol | | 0.378 |
| ethyl acetate | | 0.794 |
| sodium sulfite | | 0.090 |
| triethanolamine | | 0.300 |
| ethyl alcohol | | 19.00 |
| Polymer JR | | 0.500 |
| Emulphogene BC 720 | | 0.053 |
| perfume | | 0.013 |
| stearyldimethylbenzylammonium chloride | | 0.067 |
| E.D.T.A. disodium salt | | 0.100 |
| Brij 35 | | 0.04 |
| water | q.s. | 100.0 |

To 93 g. of above composition, 7 g. of a propellant blend of 152A/114/12 (30/35/35) is added to obtain a quick breaking aerosol foam.

The composition is applied for 10 to 30 minutes to gray hair, followed directly by rinsing or shampooing. After daily application for 10 days, to gray hair, a natural looking medium drab brown shade is obtained.

EXAMPLE 2, GEL a. The triol is prepared by weighing 3.42 g. 1,2,4-benzenetriacetate, 50 g. ethyl alcohol (95%), 1 g. conc. sulfuric acid into a container which should have little or no headspace remaining. Cap the container and place in a 50° oven for 18 hours (approx.). A clear solution will result containing 1.71 g. triol, 3.59 g. ethyl acetate and excess alcohol. Set aside until step (e).
b. Disperse 10 g. of Carbopol 941 in 750 g. cold water with vigorous agitation, continue agitation raising temperature to 40°-50° C, cool down to room temperature when smooth dispersion is obtained, continue stirring.
c. Add 4 g. BHE and 1.2 g. sodium sulfite.
d. Mix 0.13 g. perfume into 0.4 g. Brij 35 and add to main solution.
e. Add triol solution.
f. Add 43 g. triethanolamine, and adjust pH with triethanolamine and sulfuric acid to 7.9-8.1.
g. Q.S. with water to 1,000 g. to form a soft gel.

The composition after being applied twice a day for 2 days to gray hair gives a natural-looking drab brown shade. In an alternative procedure, the above composition after being applied daily for about 10 days to gray hair gives a natural-looking drab brown shade.

EXAMPLE 3, LIQUID a. The triol is prepared by weighing 2.8 g. 1,2,4-benzenetriacetate, 50 g. ethyl alcohol (95%), 1 g. conc. sulfuric acid into a container which should have little or no head-space remaining. Cap the container and place in a 50° oven for 18 hours (approx.). A clear solution will result containing 1.4 g. triol, 2.94 g. ethyl acetate and excess alcohol. Set aside until step (e).
b. Mix together 100 g. UCON LB-1715, 100 g. UCON LB-3000, 500 g. ethyl alcohol, and 200 g. water to clear blend.
c. Add 1.47 g. BHE and 1.2. g. sodium sulfite.
d. Mix 0.13 g. perfume into 0.4 g. Brij 35 and add to main solution.
e. Add triol solution.
f. Add 1 g. triethanolamine, and adjust pH with triethanolamine and sulfuric acid to 7.9 – 8.1.
g. Q.S. with water to 1,000 g.

A clear near colorless solution is obtained with the following composition.

| | | |
|---|---|---|
| 2,4,5 trihydroxytoluene | | 0.140% |
| N,N bis (2-hydroxyethyl) p-phenylene diamine sulfate | | 0.147 |
| sodium sulfite | | 0.120 |
| triethanolamine | | 0.100 |
| UCON LB-1715 | | 10.00 |
| UCON LB-3000 | | 10.000 |
| Brij 35 | | 0.04 |
| perfume | | 0.013 |
| ethyl alcohol (95%) | | 50.00 |
| ethyl acetate | | 0.294 |
| D. I. Water | to | 100.00 |

In any of the above examples the perfume may be eliminated and replaced with an equal quantity of water.

EXAMPLE 4

15.84 g. of 2,4,5-toluenetriacetate, 30 ml. of methanol and 3 m. of concentrated hydrochloric acid were stored, at room temperature in a stoppered flask, overnight. The triacetate was thus converted to the triol with no discoloration.

7 ml. of this triol solution was employed in step (e) of Example 3, 1 and the resulting product was suitable for producing a warm brown shade on grey hair.

What is claimed is:
1. In a process for preparing a hair dye composition comprising a solution of a tinctorially effective amount of N,N-bis(2-hydroxyethyl)-p-phenylenediamine or an acid addition salt thereof and a tinctorially effective amount of a triol selected from the group consisting of 1,2,4-benzenetriol and 2,4,5-trihydroxytoluene the improvement which comprises preforming a solution containing a tinctorially effective amount of the triol by storing a triacetate of said triol at a temperature between about room temperature and 50° C for about 12 to 24 hours with ethanol in dilute sulfuric acid and then incorporating in said preformed solution water and a composition containing a tinctorially effective amount of said N,N-bis(2-hydroxyethyl)-p-phenylenediamine or an acid addition salt thereof.

2. A process according to claim 1 including the step of adjusting with a suitable alkali the pH of the composition formed by mixing said preformed solution of said triol and said N,N-bis (2-hydroxyethyl)-p-phenylenediamine or acid addition salt thereof.

3. In a process for preparing a hair dye composition comprising a solution of a tinctorially effective amount of:
a. a p-phenylenediamine of the formula

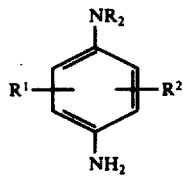

or an acid addition salt thereof; where R is hydrogen, 2-hydroxyethyl, 2-hydroxypropyl, 3-hydroxypropyl, or 2,3-dihydroxypropyl and where $R^1$ and $R^2$, which may be the same or different, are hydrogen or methyl; and b. a tinctorially effective amount of a triol selected from the group 1,2,4-benzenetriol and 2,4,5-trihydroxytoluene;

the improvement which comprises preforming a solution containing a tinctorially effective amount of the triol by storing the triacetate of said triol at a temperature between about room temperature and 50° C for about 12 to 72 hours with a lower aliphatic alcohol having from 1 to 3 carbon atoms and a concentrated inorganic mineral acid selected from the group consisting of sulfuric and hydrochloric, and then incorporating in said preformed solution water and a composition containing a tinctorially effective or an acid addition salt thereof.

4. A process according to claim 3 in which said p-phenylenediamine is selected from the group consisting of p-phenylenediamine; 2,5-diaminotoluene, N,N-bis(2-hydroxyethyl)-p-phenylenediamine; 2,6-dimethyl-p-phenylenediamine; and $N^4,N^4$-bis(2-hydroxyethyl)-2-methyl-p-phenylenediamine.

5. A process according to claim 3 including the step of adjusting the pH of the composition formed by mixing said preformed solution of said triol with said p-phenylenediamine or acid addition salt with a suitable alkali.

6. A process according to claim 3 in which from about 1 to 60 parts of said triacetate and from 0.5 to 2.0 parts of said concentrated acid are employed per 100 parts of said alcohol.

* * * * *